(12) United States Patent
Bigner et al.

(10) Patent No.: US 10,744,171 B2
(45) Date of Patent: Aug. 18, 2020

(54) SEQUENTIAL ANTI-CANCER TREATMENT

(71) Applicant: Duke University, Durham, NC (US)

(72) Inventors: Darell D. Bigner, Mebane, NC (US); Matthias Gromeier, Durham, NC (US); Annick Desjardins, Durham, NC (US); Henry S. Friedman, Durham, NC (US); Allan H. Friedman, Durham, NC (US); John H. Sampson, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 16/086,735

(22) PCT Filed: Mar. 20, 2017

(86) PCT No.: PCT/US2017/023148
§ 371 (c)(1),
(2) Date: Sep. 20, 2018

(87) PCT Pub. No.: WO2017/165266
PCT Pub. Date: Sep. 28, 2017

(65) Prior Publication Data
US 2019/0105360 A1 Apr. 11, 2019

Related U.S. Application Data

(60) Provisional application No. 62/310,874, filed on Mar. 21, 2016.

(51) Int. Cl.
*A61K 31/175* (2006.01)
*A61K 35/768* (2015.01)
(Continued)

(52) U.S. Cl.
CPC .......... *A61K 35/768* (2013.01); *A61K 9/0019* (2013.01); *A61K 31/175* (2013.01);
(Continued)

(58) Field of Classification Search
None
See application file for complete search history.

(56) References Cited

U.S. PATENT DOCUMENTS

| 5,622,705 A | 4/1997 | Morrow |
| 7,147,848 B2 | 12/2006 | Gromeier et al. |

(Continued)

FOREIGN PATENT DOCUMENTS

| JP | 2016500108 A | 1/2016 |
| WO | 2014-081937 A2 | 5/2014 |

OTHER PUBLICATIONS

International Search Report for PCT/US2017/023148, dated Jun. 29, 2017.
(Continued)

*Primary Examiner* — Michelle S Horning
(74) *Attorney, Agent, or Firm* — Banner & Witcoff, Ltd.

(57) ABSTRACT

Human clinical use of a chimeric poliovirus construct has demonstrated excellent anti-tumor effect. Sequential treatment with the virus construct followed by chemotherapy drugs increases the anti-tumor effect. Tumors of different types are susceptible to the combination treatment, including but not limited to melanoma, glioblastoma, renal cell carcinoma, prostate cancer, breast cancer, lung cancer, medulloblastoma, and colorectal cancer.

24 Claims, 9 Drawing Sheets

(51) Int. Cl.
*A61K 31/495* (2006.01)
*A61K 45/06* (2006.01)
*A61P 35/00* (2006.01)
*A61K 9/00* (2006.01)
*C12N 15/63* (2006.01)

(52) U.S. Cl.
CPC ............ *A61K 31/495* (2013.01); *A61K 45/06* (2013.01); *A61P 35/00* (2018.01); *C12N 15/63* (2013.01); *C12N 2770/32332* (2013.01); *C12N 2770/32371* (2013.01); *C12N 2840/203* (2013.01); *Y02A 50/465* (2018.01)

(56) References Cited

U.S. PATENT DOCUMENTS 8,066,983 B2  11/2011  Wimmer et al.
2011/0318430 A1* 12/2011 Meruelo ............ A61K 31/337
                                                    424/649

OTHER PUBLICATIONS

Morimoto, K., et al., 'Interaction of cancer cells with platelets mediated by Necl-5/poliovirus receptor enhances cancer cell metastasis to the lungs', Oncogene, 2008, vol. 27, pp. 264-273.
Oct. 31, 2019—(EP) Extended Search Report—App 17770887.2.
Goetz et al. "Preparing an oncolytic poliovirus recombinant for clinical application against glioblastoma multiforme" Cytokine & Growth Factor Reviews, 21 (2010) 193-203.
Chumakov et al. "Oncolytic Enteroviruses" Molecular Biology, vol. 45, No. 5, Oct. 9, 2012, pp. 639-650.
Natsume et al. "Novel Strategies in Chemotherapy for Gliomas" Japanese Journal of Neurosurgery, 2015, pp. 386-398.
Nov. 8, 2019—(JP) Office Action—App 2018-549578.

* cited by examiner

TRAMPC2 PVSRIPO TMZ Combination Experiment

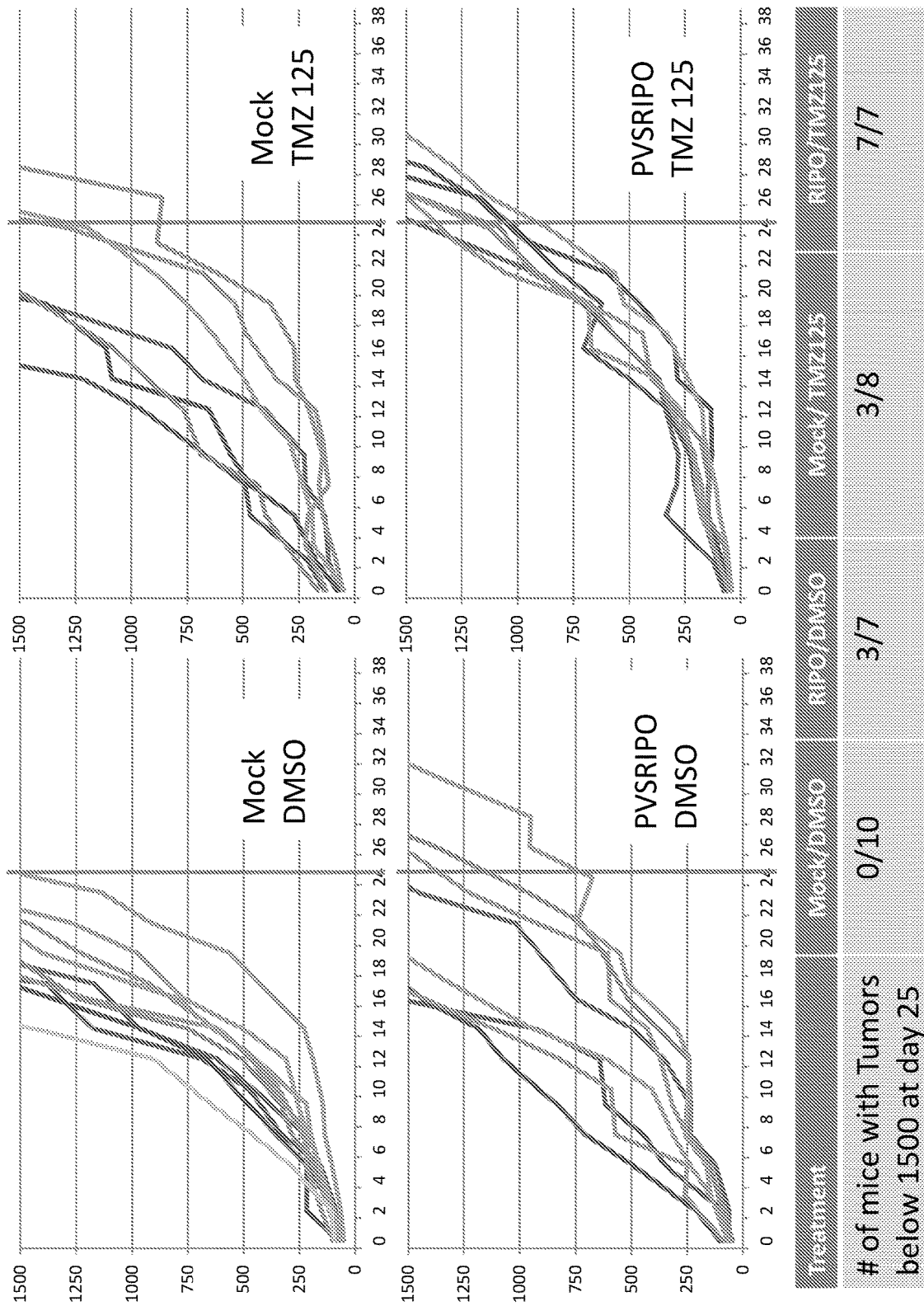

SEQUENTIAL ANTI-CANCER TREATMENT

SEQUENTIAL ANTI-CANCER TREATMENT

This invention was made using funds provided by the United States government. The U.S. government retains certain rights according to the terms of grants from the National Institutes of Health CA154291, CA197264. The content of U.S. patent application Ser. No. 14/646,233 filed May 20, 2015 is expressly incorporated herein.

TECHNICAL FIELD OF THE INVENTION

This invention is related to the area of anti-tumor therapy. In particular, it relates to oncolytic virus anti-tumor therapy.

BACKGROUND OF THE INVENTION

PVS-RIPO is an oncolytic poliovirus (PV) recombinant. It consists of the live attenuated type 1 (Sabin) PV vaccine containing a foreign internal ribosomal entry site (IRES) of human rhinovirus type 2 (HRV2). The IRES is a cis-acting genetic element located in the 5' untranslated region of the PV genome, mediating viral, $m^7G$-cap-independent translation. The virus has shown exciting signs of efficacy in humans Nonetheless there is a continuing need in the art to identify and develop anti-cancer treatments that are more effective and that are effective for more humans, particularly for patients with brain tumors.

SUMMARY OF THE INVENTION

According to one aspect of the invention a method of treating a tumor in a patient is provided. A chimeric poliovirus construct is administered to the patient. The construct comprises a Sabin type I strain of poliovirus with a human rhinovirus 2 (HRV2) internal ribosome entry site (IRES) in said poliovirus' 5' untranslated region between said poliovirus' cloverleaf and said poliovirus' open reading frame. A chemotherapy agent is administered to the patient when growth of the tumor progresses after poliovirus administration, or on a schedule, regardless of progression.

According to another aspect of the invention a kit is provided for treating a tumor with a first agent followed by a second agent after a gap of at least 3 month. The kit comprises as a first agent a chimeric poliovirus construct comprising a Sabin type I strain of poliovirus with a human rhinovirus 2 (HRV2) internal ribosome entry site (IRES) in said poliovirus' 5' untranslated region between said poliovirus' cloverleaf and said poliovirus' open reading frame. The kit comprises as a second agent a chemotherapy agent.

Also provided as an additional aspect of the invention is a composition for treating a tumor prior to treatment with a chemotherapeutic agent. The composition comprises a chimeric poliovirus construct comprising a Sabin type I strain of poliovirus with a human rhinovirus 2 (HRV2) internal ribosome entry site (IRES) in said poliovirus' 5' untranslated region between said poliovirus' cloverleaf and said poliovirus' open reading frame.

Additionally provided as an additional aspect of the invention is a composition for treating a tumor subsequent to treatment with a chimeric poliovirus construct comprising a Sabin type I strain of poliovirus with a human rhinovirus 2 (HRV2) internal ribosome entry site (IRES) in said poliovirus' 5' untranslated region between said poliovirus' cloverleaf and said poliovirus' open reading frame. The composition comprises a chemotherapeutic agent.

These and other aspects which will be apparent to those of skill in the art upon reading the specification provide the art with new therapeutic regimens for treating cancer.

BRIEF DESCRIPTION OF THE DRAWINGS

FIG. 7B shows percentage survival results in a Kaplan-Meier plot. FIG. 7C shows the results of the average tumor size over time.

FIG. 8—The experimental results of FIG. 7C are shown for individual mice in the cohorts in FIG. 8. The results for number of individual mice with tumors below 1500 mm$^3$ at day 25 are tabulated below.

DETAILED DESCRIPTION OF THE INVENTION

Figure 1:
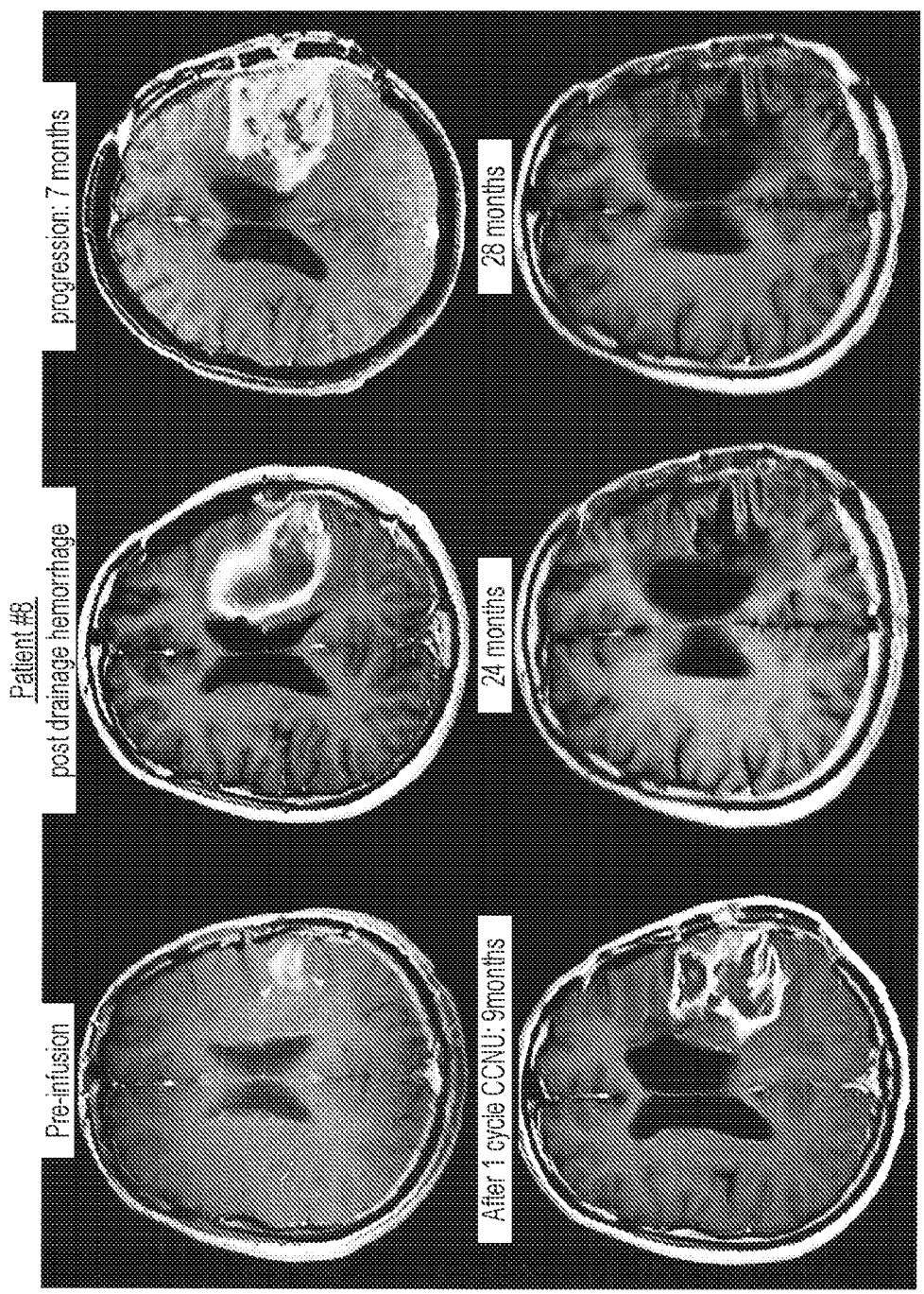
FIG. 1—Patient #8 brain scans at times: pre-infusion of PVSRIPO, post drainage of hemorrhage, 7 months after PVSRIPO infusion, at time of first observed progression, at 9 months, after 1 cycle of lomustine (CCNU), at 24 months, and at 28 months.
Figure 2:
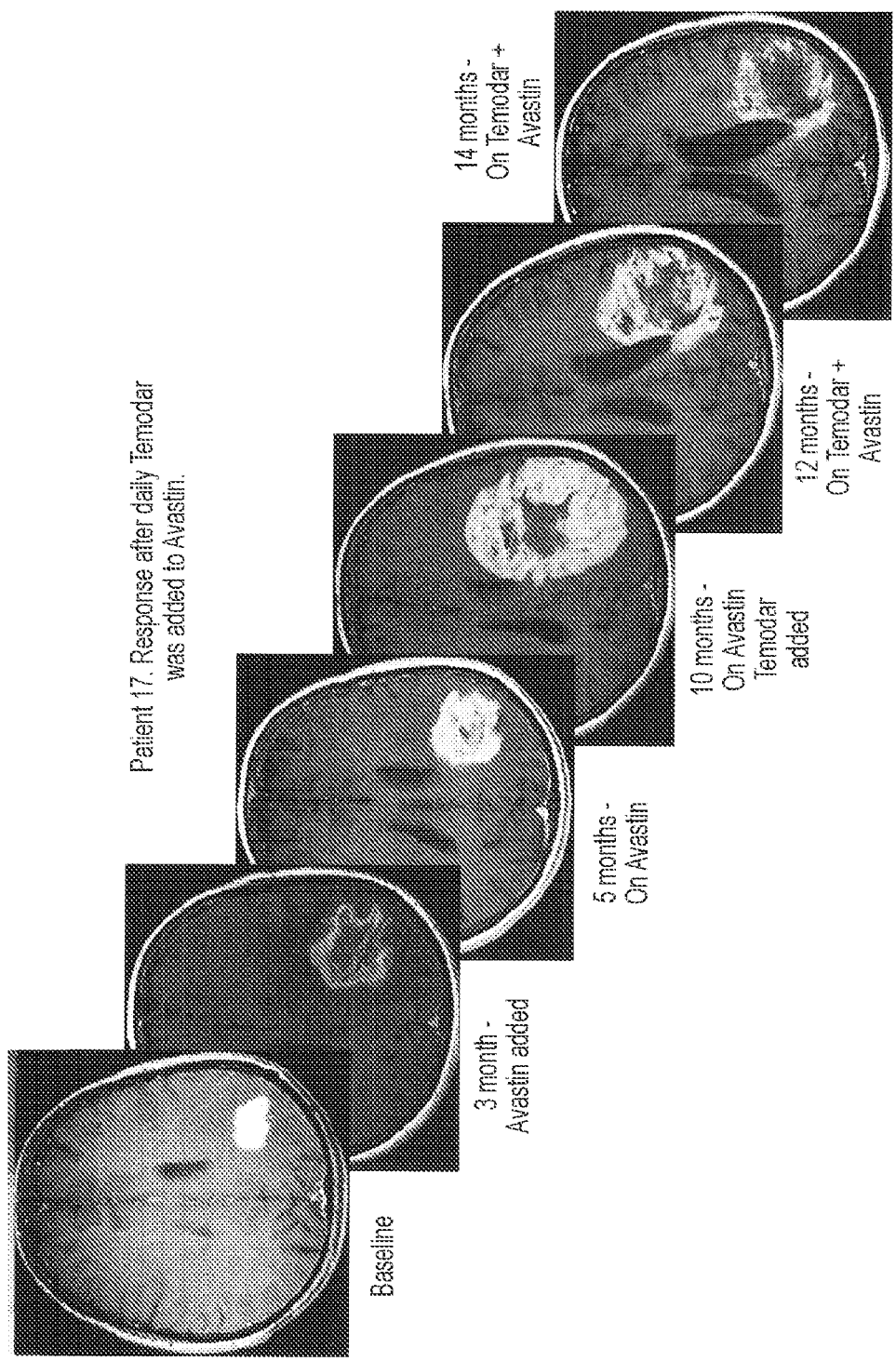
FIG. 2—Patient #17 showing response after daily temodar was added to avastin. Brain scans at base line, 3 month, 5 months, 10 months, 12 months, and 14 months. Daily Temodar (temozolomide) was added to avastin regimen at 10 months.
Figure 3:
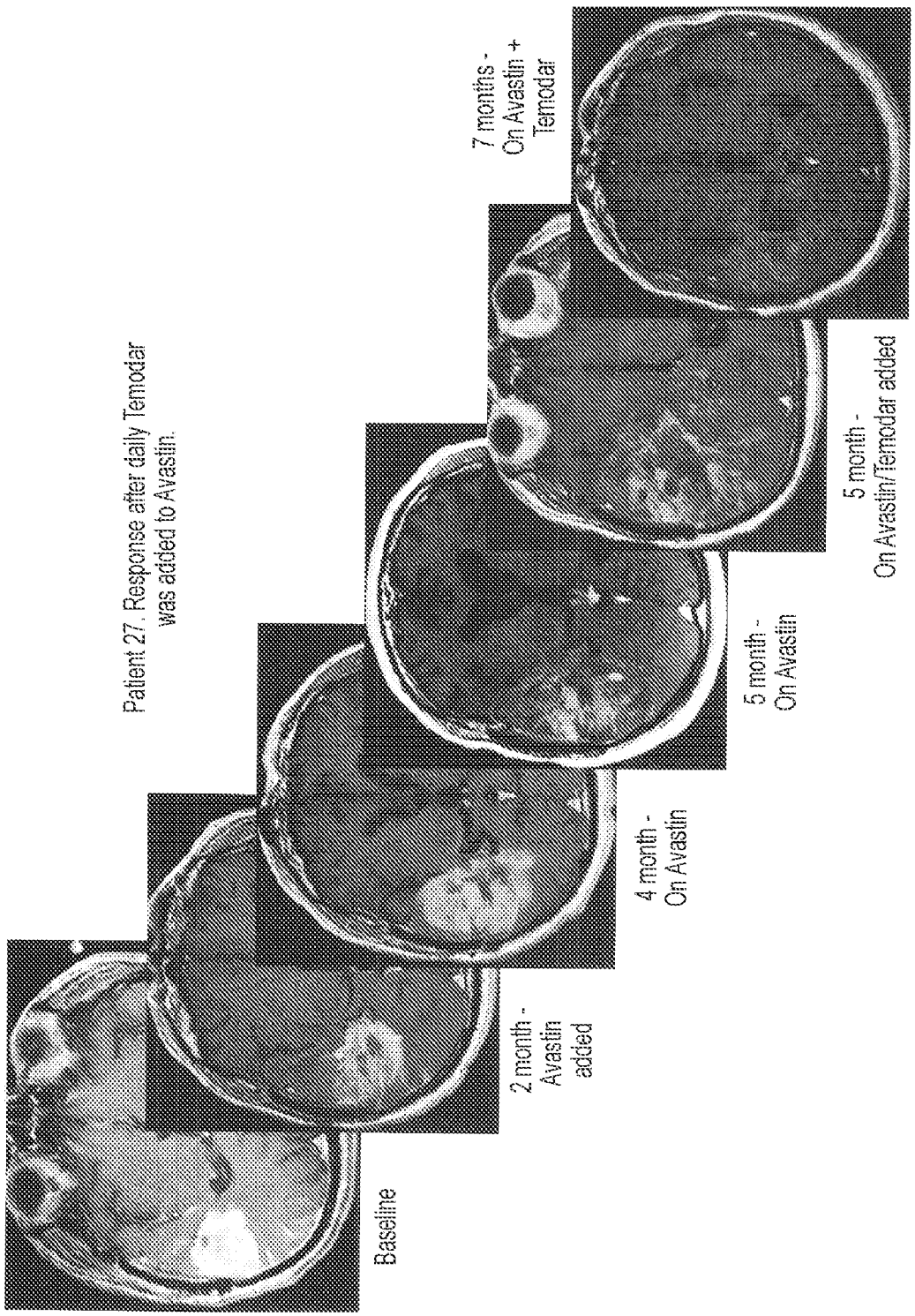
FIG. 3—Patient #27 showing response after daily Temodar was added to Avastin. Brain scans at baseline, 2 months, 4 months, 5 months, and 7 months. Avastin was added at 2 months and Temodar was added at 5 months.
Figure 4:
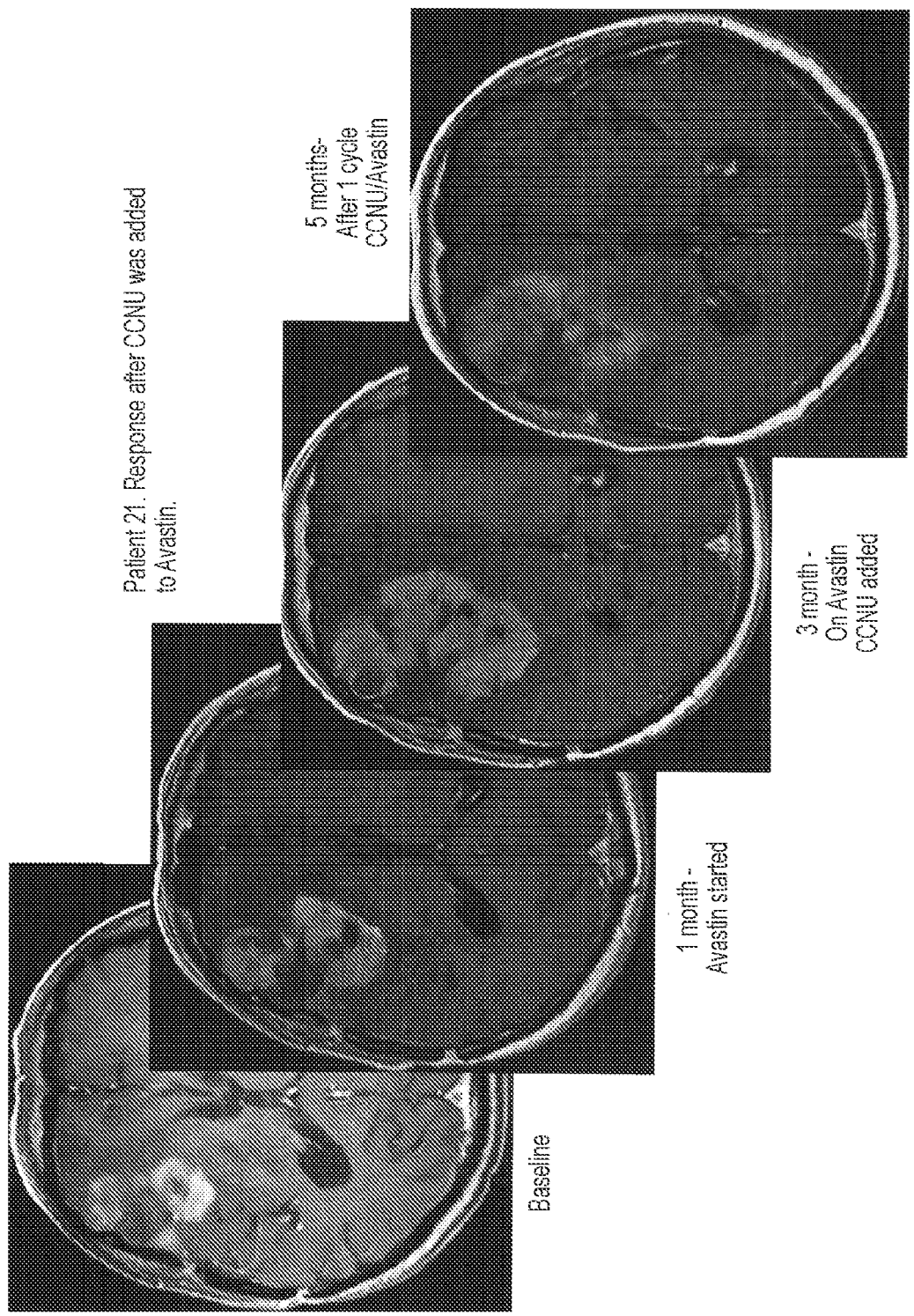
FIG. 4—Patient 21. Response after CCNU (lomustine) was added to Avastin. Brain scans shown at baseline, 1 month, 3 months and 5 months. Avastin was started at 1 month. At 3 months CCNU was added.
Figure 5:
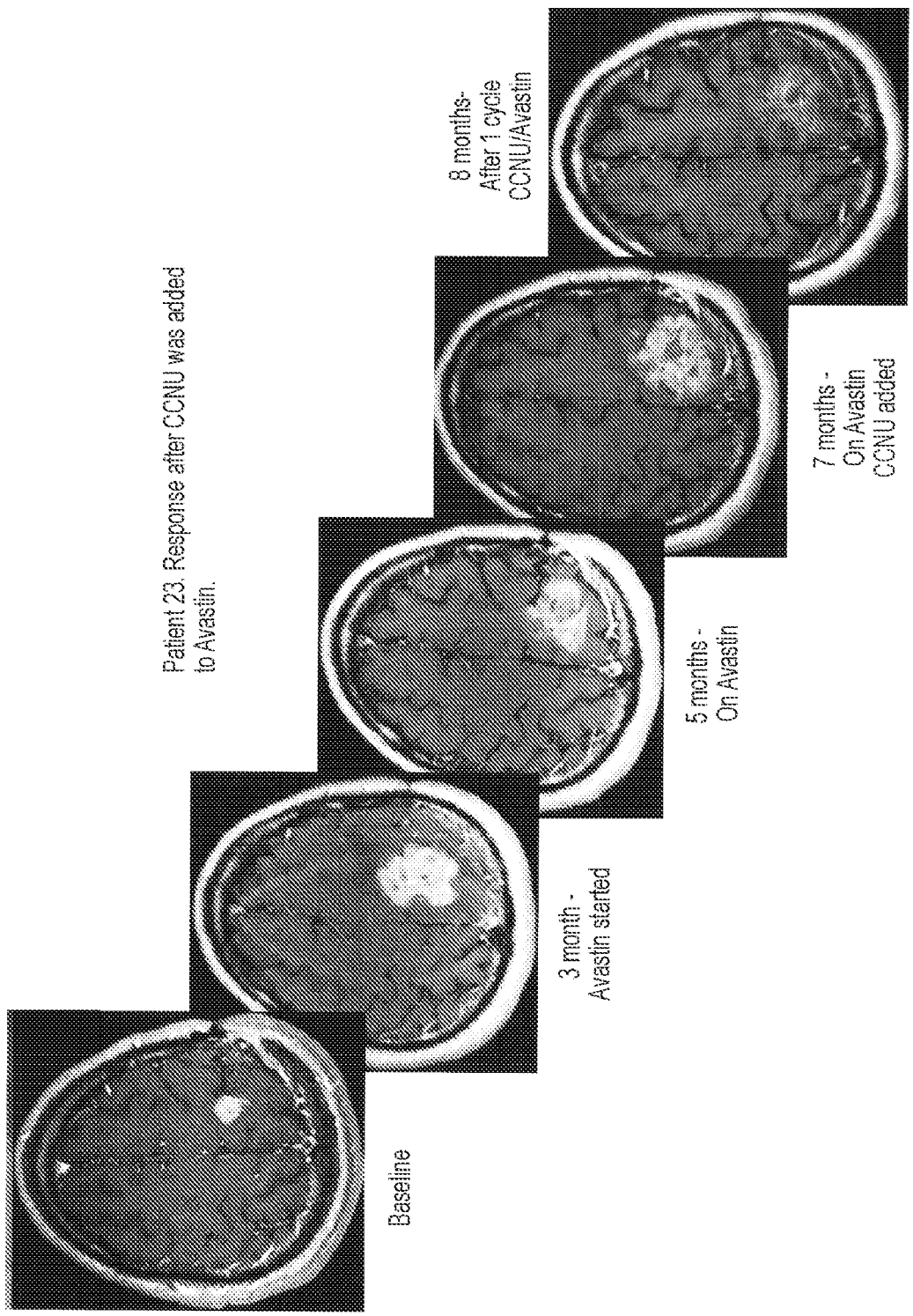
FIG. 5—Patient #23. Response after CCNU was added to Avastin. Brain scans shown at baseline, 3 months, 5 months, 7 months, and 8 months. Avastin was started at 3 months. CCNU was added at 7 months.
Figure 6:
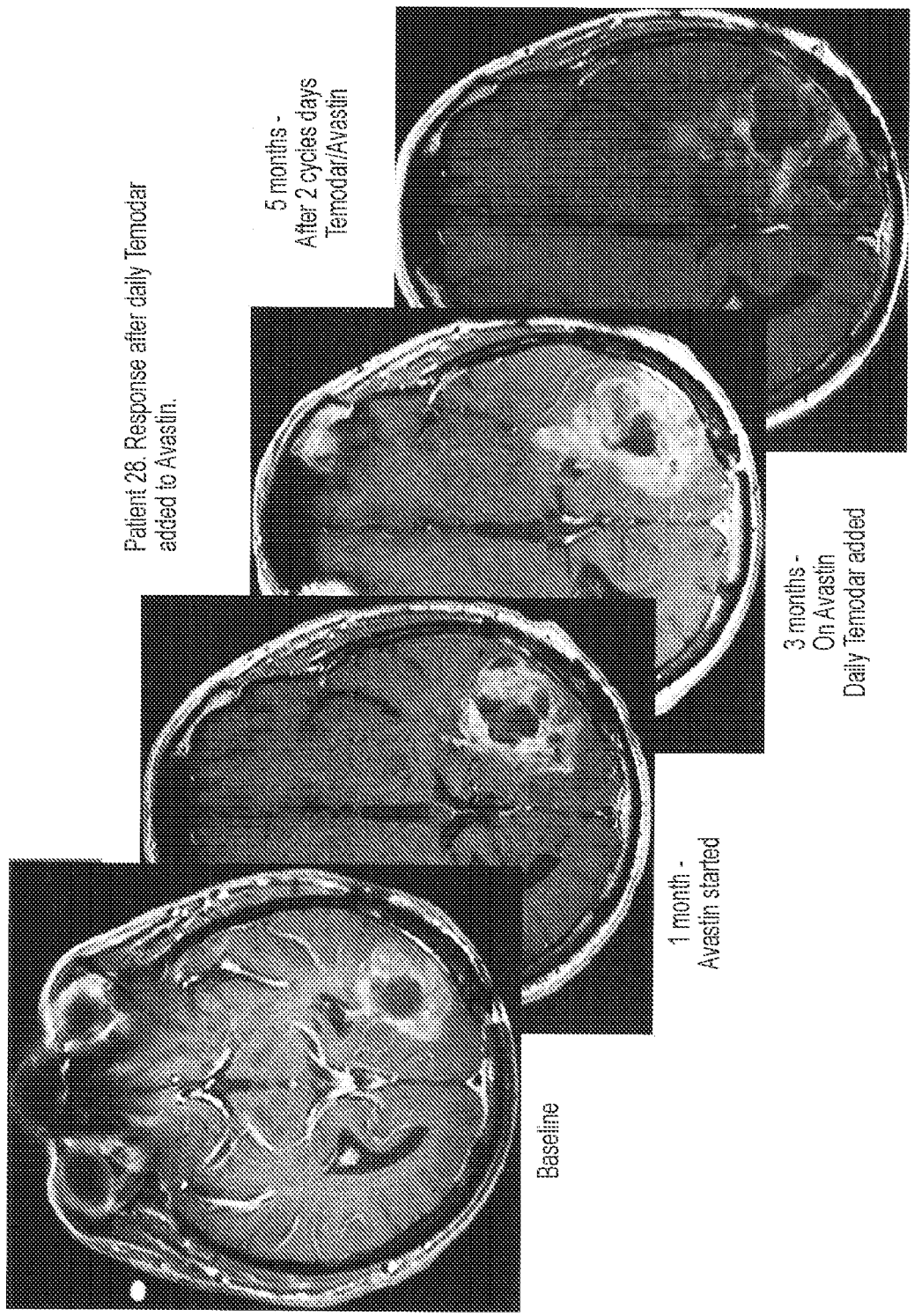
FIG. 6—Patient #28. Response after daily Temodar added to Avastin. Brain scans shown at baseline, 1 month, 3 months, and 5 months. Avastin was started at 1 month. Daily Temodar was added at 3 months.
Figure 7A:
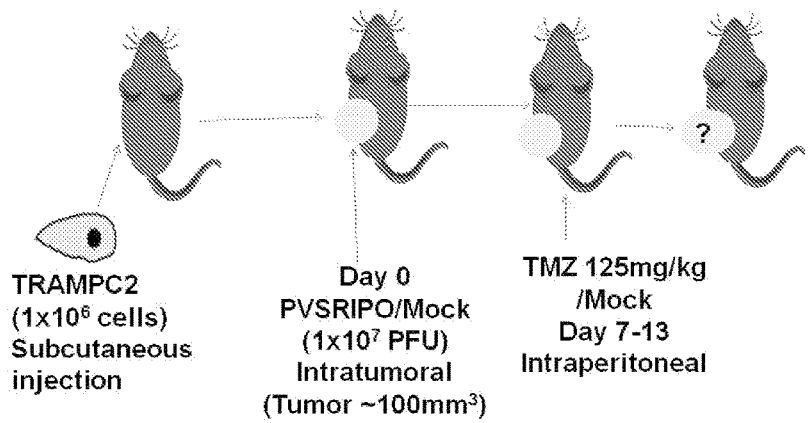
FIG. 7A-7C—TRAMP-C2, a syngeneic mouse prostate cancer model (transduced with human poliovirus receptor, CD155) in CD155-transgenic mice was treated as shown in FIG. 7A with PVSRIPO on Day 0 and with temozolomide (TMZ) on days 7-13. This model is commonly used as a negative control for cancer immunotherapy. TRAMP is confirmed to have not a single antigenic epitope that could be recognized by the immune system. Therefore, nothing really works in this model through immunotherapy. We believe that this is the reason that PVSRIPO only has a minimal effect on TRAMP. We deliberately chose this highly resistant model to test synergy of TMZ with PVSRIPO.
Figure 7B:
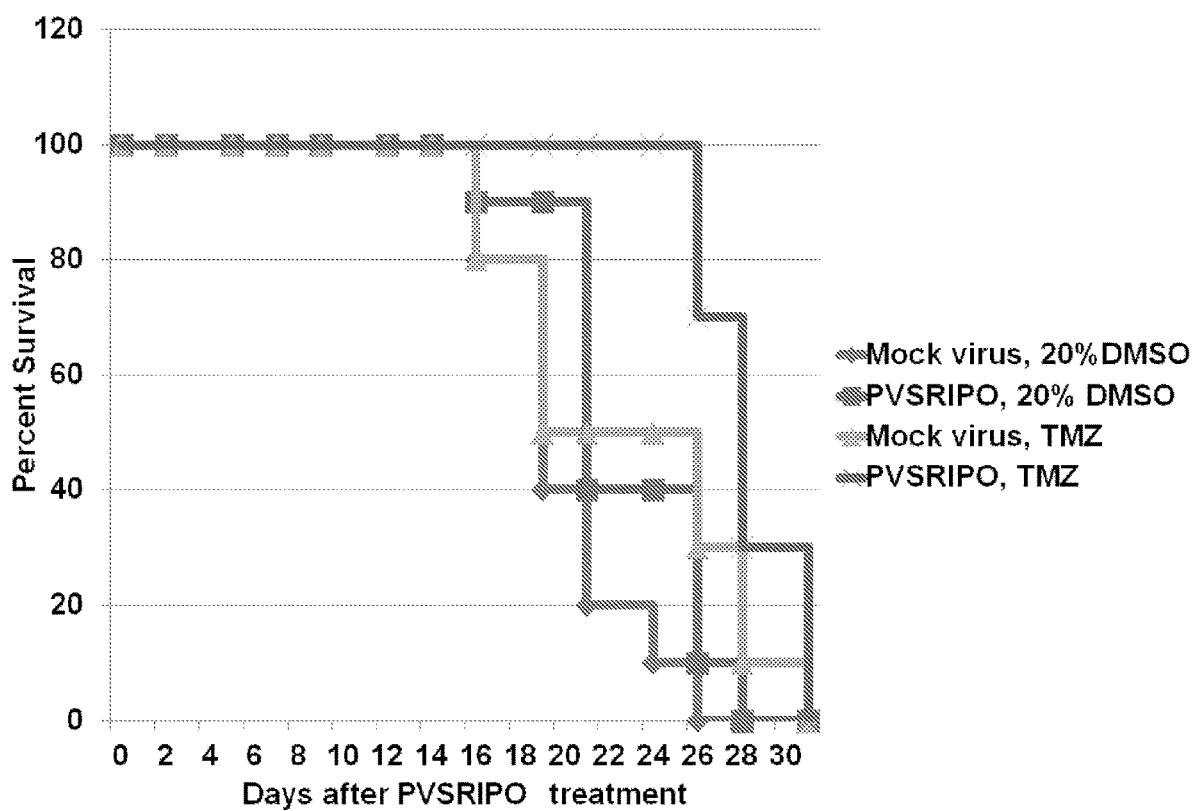
Figure 7C:
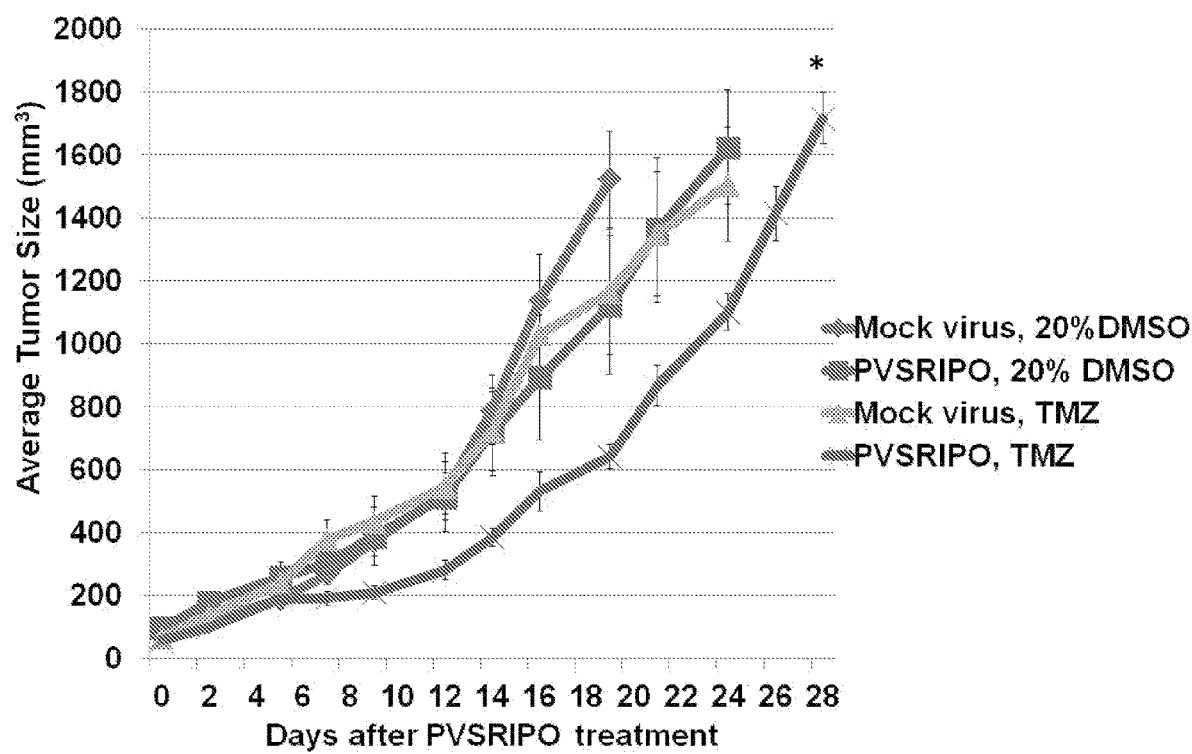

The inventors have developed a method in which the efficacy of PVSRIPO chimeric poliovirus construct is increased and/or prolonged by subsequent administration of a chemotherapeutic agent. The effects are synergistic. While applicants do not wish to be bound by any particular mechanism of action, the increased/prolonged efficacy may be due to the ability of the chemotherapeutic agents to lymphodeplete. Lymphodepletion may remove competition at the surface of antigen presenting cells, enhance the availability of cytokines which augment T cell activity, deplete regulatory T cells, enhance immune priming and presentation, enhance antigen expression, and/or enhance targets for immune eradication.

Chemotherapy is preferably administered well after the initial effects of the PVSRIPO chimeric poliovirus construct have been observed. The administration may be at least 2 months, 3 months, 4 months, 5 months, 6 months, 7 months, 10 months, 12, months, 18 months, or 24 months after PVSRIPO delivery. The chemotherapy may be administered continuously or in cycles with gaps in the treatment to permit lymphocyte recovery, for example.

Suitable chemotherapy drugs are those that are lymphodepleting. These include classical alkylating agents such as Nitrogen mustards, including Cyclophosphamide, Mechlorethamine or MUSTARGEN™ (mustine (HN2)), Uramustine or uracil mustard, Melphalan, Chlorambucil, Ifosfamide, and Bendamustine. These also include the Nitrosoureas, such as Carmustine, Lomustine, and Streptozocin. These also include the Alkyl sulfonates, such as Busulfan. Platinum-based chemotherapeutic drugs (termed platinum analogues) act in a similar manner and may be used similarly. These agents do not have an alkyl group, but nevertheless damage DNA. They permanently coordinate to DNA to interfere with DNA repair, so they are sometimes described as "alkylating-like." These include Cisplatin, Carboplatin, Nedaplatin, Oxaliplatin, Satraplatin, and Triplatin tetranitrate. Additionally, nonclassical alkylating agents may be used, including but not limited to procarbazine, altretamine, triazenes such as dacarbazine, mitozolomide, and temozolomide.

Any technique for directly administering the viral preparation to the tumor may be used. Direct administration does not rely on the blood vasculature to access the tumor. The preparation may be painted on the surface of the tumor, injected into the tumor, instilled in or at the tumor site during surgery, infused into the tumor via a catheter, etc. One particular technique which may be used is convection enhanced delivery.

Metronomic chemotherapy, which refers to the frequent administration of chemotherapeutics at doses significantly below the maximum tolerated dose without prolonged drug-free breaks, may be used. For example, a standard non-metronomic regimen with temozolomide consists of 150 to 200 mg/m$^2$ daily for 5 consecutive days repeated every 4 weeks. Metronomic regimen may be, for example, a dose of 50 mg/m$^2$/day daily for 2 or 3 months. Similar low dose regimens with other chemotherapeutic agents may be used. Low dose regimens may also be used with standard timing. Standard dose and timing therapy may also be used.

Any human tumor can be treated, including both pediatric and adult tumors. The tumor may be in any organ, for example, brain, prostate, breast, lung, colon, and rectum, Various types of tumors may be treated, including, for example, glioblastoma, medulloblastomas, carcinoma, adenocarcinoma, etc. Other examples of tumors include, adrenocortical carcinoma, anal cancer, appendix cancer, grade I (anaplastic) astrocytoma, grade II astrocytoma, grade III astrocytoma, grade IV astrocytoma, atypical teratoid/rhabdoid tumor of the central nervous system, basal cell carcinoma, bladder cancer, breast sarcoma, bronchial cancer, bronchoalveolar carcinoma, cervical cancer, craniopharyngioma, endometrial cancer, endometrial uterine cancer, ependymoblastoma, ependymoma, esophageal cancer, esthesioneuroblastoma, Ewing's sarcoma, extracranial germ cell tumor, extragonadal germ cell tumor, extrahepatic bile duct cancer, fibrous histiocytoma, gall bladder cancer, gastric cancer, gastrointestinal carcinoid tumor, gastrointestinal stromal tumor, gestational trophoblastic tumor, gestational trophoblastic tumor, glioma, head and neck cancer, hepatocellular cancer, Hilar cholangiocarcinoma, hypopharyngeal cancer, intraocular melanoma, islet cell tumor, Kaposi sarcoma, Langerhans cell histiocytosis, large-cell undifferentiated lung carcinoma, laryngeal cancer, lip cancer, lung adenocarcinoma, malignant fibrous histiocytoma, medulloepithelioma, melanoma, Merkel cell carcinoma, mesothelioma, endocrine neoplasia, nasal cavity cancer, nasopharyngeal cancer, neuroblastoma, oral cancer, oropharyngeal cancer, osteosarcoma, ovarian clear cell carcinoma, ovarian epithelial cancer, ovarian germ cell tumor, pancreatic cancer, papillomatosis, paranasal sinus cancer, parathyroid cancer, penile cancer, pharyngeal cancer, pineal parenchymal tumor, pineoblastoma, pituitary tumor, pleuropulmonary blastoma, renal cell cancer, respiratory tract cancer with chromosome 15 changes, retinoblastoma, rhabdomyosarcoma, salivary gland cancer, small cell lung cancer, small intestine cancer, soft tissue sarcoma, squamous cell carcinoma, squamous non-small cell lung cancer, squamous neck cancer, supratentorial primitive neuroectodermal tumor, supratentorial primitive neuroectodermal tumor, testicular cancer, throat cancer, thymic carcinoma, thymoma, thyroid cancer, cancer of the renal pelvis, urethral cancer, uterine sarcoma, vaginal cancer, vulvar cancer, and Wilms tumor.

Optionally, patients may be stratified on the basis of NECL5 expression. This can be assayed at the RNA or protein level, using probes, primers, or antibodies, for example. The NECL5 expression may guide the decision to treat or not treat with the chimeric poliovirus of the present invention. The NECL5 expression may also be used to guide the aggressiveness of the treatment, including the dose, frequency, and duration of treatments.

Treatment regimens may include, in addition to delivery of the chimeric poliovirus construct, surgical removal of the tumor, surgical reduction of the tumor, chemotherapy biological therapy, and radiotherapy. These modalities are standard of care in many disease states, and the patient need not be denied the standard of care. The chimeric poliovirus may be administered before, during, or after the standard of care. The chimeric poliovirus may be administered after failure of the standard of care.

Kits may comprise, in a single divided or undivided container, either or both the chimeric poliovirus construct PVSRIPO as well as a chemotherapeutic agent. If both are provided in the kit, the two may be in separate vessels or in a single vessel in admixture. Instructions for administration may be included. Optionally, an antibody for testing NECL5 expression in the patient is a component of the kit.

While applicants do not wish to be bound by any particular mechanism of action, it is believed that multiple mechanisms may contribute to the efficacy of PVSRIPO. These include lysis of cancer cells, recruitment of immune cells, and specificity for cancer cells. Moreover, the virus is neuro-attenuated. The mechanism of enhancement/prolongation by a chemotherapy agent may also be multifactorial.

The above disclosure generally describes the present invention. All references disclosed herein are expressly incorporated by reference. A more complete understanding can be obtained by reference to the following specific examples, which are provided herein for purposes of illustration only, and are not intended to limit the scope of the invention.

EXAMPLE

As of Feb. 23, 2016, of the 20 patients treated on $5 \times 10^7$ TCID$_{50}$ of PVSRIPO, five patients had imaging concerning for disease progression, as well as clinical decline, following PVSRIPO infusion despite being on bevacizumab to help control the cerebral inflammation. Three patients were continued on bevacizumab and initiated on metronomic daily temozolomide at 50 mg/m²/day, with a goal of treating the tumor and helping in controlling the cerebral inflammation. Two patients had significant improvement on imaging at the first MRI follow-up and clinically significant improvement in their functional status. The third patient had a slight improvement on imaging, but failed to improve clinically and thus, the patient elected to proceed with comfort care and is now deceased. For two of the five patients, lomustine was added to bevacizumab. Both patients showed significant imaging and clinical improvement after the first six weeks of therapy (one cycle of lomustine), which is unusual for lomustine. However, one patient decided months later to discontinue lomustine and is now deceased. Three of the five patients remain alive, two on metronomic daily temozolomide and bevacizumab and one on lomustine and bevacizumab, continue on therapy and are doing well.

One patient treated with $1.0 \times 10^{10}$ TCID$_{50}$ of PVSRIPO experienced a dose limiting toxicity due to intracerebral hemorrhage at the time of catheter removal. The hemorrhage was drained, as well as possibly a significant amount of PVSRIPO. The patient demonstrated disease progression on imaging, confirmed to be recurrent glioblastoma (WHO grade IV) by biopsy, 7 months post PVSRIPO infusion. The patient was then initiated on lomustine and demonstrated significant clinical and imaging response after one cycle of lomustine. The patient completed nine cycles of lomustine 10 months ago and remains disease free (complete tumor disappearance) more 32 months post PVSRIPO infusion. It is to note that it is believed that the patient received less than the planned dose of PVSRIPO ($1.0 \times 10^{10}$ TCID$_{50}$) given the need to drain the hemorrhage, also the patient never received bevacizumab with the lomustine, given the concern for repeat cerebral hemorrhage.

REFERENCES

The disclosure of each reference cited is expressly incorporated herein.
1. Castriconi R, A Daga, A Dondero, G Zona, P L Poliani, et al. 2009. NK cells recognize and kill human glioblastoma cells with stem cell-like properties J Immunol 182:3530-39.
2. de Breyne S, Y Yu, A Unbehaun, T V Pestova, C U Hellen. 2009. Direct functional interaction of initiation factor eIF4G with type 1 internal ribosomal entry sites. Proc Natl Acad Sci USA 106:9197-202.
3. Dobrikova E Y, T Broadt, J Poiley-Nelson, X Yang, G Soman, et al. 2008. Recombinant oncolytic poliovirus eliminates glioma in vivo without genetic adaptation to a pathogenic phenotype. Mol Ther 16:1865-72.
4. Dobrikova E Y, C Goetz, R W Walters, S K Lawson, J O Peggins, et al. 2012. Attenuation of neurovirulence, biodistribution, and shedding of a poliovirus:rhinovirus chimera after intrathalamic inoculation in Macaca fascicularis. J Virol 86:2750-9.
5. Erickson B M, N L Thompson, D C Hixson. 2006. Tightly regulated induction of the adhesion molecule necl-5/CD155 during rat liver regeneration and acute liver injury. Hepatology 43:325-34.
6. Goetz C, E Dobrikova, M Shveygert, M Dobrikov, M Gromeier. 2011. Oncolytic poliovirus against malignant glioma. Future Virol 6:1045-58.
7. Goetz, C, R G Everson, L Zhang, M Gromeier. 2010. MAPK signal-integrating kinase controls cap-independent translation and cell type-specific cytotoxicity of an oncolytic poliovirus. Mol Ther 18:1937-46.
8. Gromeier M, L Alexander, E Wimmer 1996. Internal ribosomal entry site substitution eliminates neurovirulence in intergeneric poliovirus recombinants. Proc Natl Acad Sci USA 93:2370-5.
9. Gromeier M, B Bossert, M Arita, A Nomoto, E Wimmer 1999. Dual stem loops within the poliovirus internal ribosomal entry site control neurovirulence. J Virol 73:958-64.
10. Gromeier M, S Lachmann, M R Rosenfeld, P H Gutin, E Wimmer. 2000. Intergeneric poliovirus recombinants for the treatment of malignant glioma. Proc Natl Acad Sci USA 97:6803-8.
11. Gromeier M, D Solecki, D D Patel, E Wimmer. 2000. Expression of the human poliovirus receptor/CD155 gene during development of the central nervous system: implications for the pathogenesis of poliomyelitis. Virology 273:248-57.
12. Iwasaki A, R Welker, S Mueller, M Linehan, A Nomoto, et al. 2002. Immunofluorescence analysis of poliovirus receptor expression in Peyer's patches of humans, primates, and CD155 transgenic mice: implications for poliovirus infection. J Infect Dis 186:585-92.
13. Joshi S, S Kaur, A J Redig, K Goldsborough, K David, et al. 2009. Type I IFN-dependent activation of Mnk1 and its role in the generation of growth inhibitory responses. Proc Natl Acad Sci USA 106:12097-102.
14. Masson D, A Jarry, B Baury, P Blanchardie, C Laboisse, et al. 2001. Overexpression of the CD155 gene in human colorectal carcinoma. Gut 49:236-40.
15. Merrill M K, G Bernhardt, J H Sampson, C J Wikstrand, D D Bigner, et al. 2004. Poliovirus receptor CD155-targeted oncolysis of glioma. Neuro-oncol 6:208-17.
16. Merrill M K, E Y Dobrikova, M Gromeier. 2006. Cell-type-specific repression of internal ribosome entry site activity by double-stranded RNA-binding protein 76. J Virol 80:3147-56.
17. Merrill M K, M Gromeier. 2006. The double-stranded RNA binding protein 76:NF45 heterodimer inhibits translation initiation at the rhinovirus type 2 internal ribosome entry site. J Virol 80:6936-42.
18. Nakai R, Y Maniwa, Y Tanaka, W Nishio, M Yoshimura, et al. 2010. Overexpression of Necl-5 correlates with unfavorable prognosis in patients with lung adenocarcinoma. Cancer Sci 101:1326-30.
19. Neplioueva V, E Y Dobrikova, N Mukherjee, J D Keene, M Gromeier. 2010. Tissue type-specific expression of the DRBP76 and genome-wide elucidation of its target mRNAs. PloS One 5:e11710.
20. Ochiai H, S A Campbell, G E Archer, T A Chewning, E Dragunsky, et al. 2006. Targeted therapy for glioblastoma multiforme neoplastic meningitis with intrathecal delivery of an oncolytic recombinant poliovirus. Clin Can Res 12:1349-54.
21. Ochiai H, S A Moore, G E Archer, T Okamura, T A Chewning, et al. 2004. Treatment of intracerebral neoplasia and neoplastic meningitis with regional delivery of oncolytic recombinant poliovirus. Clin Can Res 10:4831-8.
22. Takai Y, J Miyoshi, W Ikeda, H Ogita. 2008. Nectins and nectin-like molecules: roles in contact inhibition of cell movement and proliferation. Nat Rev Mol Cell Biol 9:603-15.

23. Toyoda H, J Yin, S Mueller, E Wimmer, J Cello. 2007. Oncolytic treatment and cure of neuroblastoma by a novel attenuated poliovirus in a novel poliovirus-susceptible animal model. Cancer Res 67:2857-64.
24. Wahid R, M J Cannon, M Chow. 2005. Dendritic cells and macrophages are productively infected by poliovirus. J Virol 79:401-9.

The invention claimed is:

1. A method of treating a progressing tumor in a patient, comprising:
   administering to the patient with a progressing tumor a chimeric poliovirus construct comprising a Sabin type I strain of poliovirus with a human rhinovirus 2 (HRV2) internal ribosome entry site (IRES) in said poliovirus' 5' untranslated region between said poliovirus' cloverleaf and said poliovirus' open reading frame, wherein the patient has been previously treated with a lymphodepleting chemotherapeutic agent; and
   administering a lymphodepleting chemotherapeutic agent to the patient when growth of the tumor progresses after the chimeric poliovirus construct is administered.

2. The method of claim 1 wherein the lymphodepleting chemotherapeutic agent causes transient lymphopenia.

3. The method of claim 1 wherein the chemotherapeutic agent is an alkylating agent.

4. The method of claim 1 wherein the chemotherapeutic agent is lomustine.

5. The method of claim 1 wherein the chemotherapeutic agent is temozolomide.

6. The method of claim 1 wherein the chemotherapeutic agent is administered according to a metronomic schedule.

7. The method of claim 6 wherein the chemotherapeutic agent is temozolomide.

8. The method of claim 1 wherein the chemotherapeutic agent is administered at least 3 months after administering of the chimeric poliovirus construct.

9. The method of claim 1 wherein the chemotherapeutic agent is administered at least 5 months after administering of the chimeric poliovirus construct.

10. The method of claim 1 wherein the chemotherapeutic agent is administered at least 7 months after administering of the chimeric poliovirus construct.

11. The method of claim 1 wherein progression of the tumor is assessed by imaging.

12. The method of claim 1 wherein progression of the tumor is assessed by clinical indices.

13. The method of claim 1 wherein the tumor is a brain tumor.

14. The method of claim 13 wherein the tumor is a glioblastoma.

15. The method of claim 13 wherein the tumor is astrocytoma or oligodendroglioma.

16. The method of claim 13 wherein the tumor is astro-oligodendroglioma.

17. The method of claim 13 wherein the tumor is medulloblastoma.

18. The method of claim 1 wherein the tumor is selected from the group consisting of renal cell carcinoma, prostate tumor, bladder tumor, esophagus tumor, stomach tumor, pancreas tumor, colorectal tumor, liver or gall bladder tumor, breast tumor, lung tumor, head and neck tumor, melanoma, and sarcoma.

19. The method of claim 1 wherein the tumor expresses NECL5 (nectin-like protein 5).

20. The method of claim 13 wherein the chimeric poliovirus construct is administered by intracerebral infusion with convection enhanced delivery.

21. The method of claim 1 which comprises the step of: prior to the step of administering the poliovirus construct, testing the tumor to ascertain that it expresses NECL5.

22. The method of claim 1 wherein the chimeric poliovirus construct is administered directly to the tumor.

23. The method of claim 1 wherein the chimeric poliovirus construct is administered when growth of the tumor progresses.

24. The method of claim 1 wherein the chimeric poliovirus construct is PVS-RIPO.

* * * * *